(12) United States Patent
Wang et al.

(10) Patent No.: US 11,600,000 B2
(45) Date of Patent: Mar. 7, 2023

(54) IMAGE PROCESSING METHOD AND SYSTEM FOR SELECTIVELY DELETING LABEL ON MEDICAL IMAGE

(71) Applicant: HTC Corporation, Taoyuan (TW)

(72) Inventors: Hao-Jen Wang, Taoyuan (TW); Fu-Chieh Chang, Taoyuan (TW); Edzer Lienson Wu, Taoyuan (TW)

(73) Assignee: HTC Corporation, Taoyuan (TW)

( * ) Notice: Subject to any disclaimer, the term of this patent is extended or adjusted under 35 U.S.C. 154(b) by 183 days.

(21) Appl. No.: 17/131,788

(22) Filed: Dec. 23, 2020

(65) Prior Publication Data
US 2021/0192735 A1 Jun. 24, 2021

Related U.S. Application Data

(60) Provisional application No. 62/952,498, filed on Dec. 23, 2019.

(51) Int. Cl.
*G06K 9/00* (2022.01)
*G06T 7/00* (2017.01)
(Continued)

(52) U.S. Cl.
CPC ........... *G06T 7/0014* (2013.01); *G16H 30/20* (2018.01); *G16H 30/40* (2018.01); *A61B 5/0066* (2013.01);
(Continued)

(58) Field of Classification Search
CPC ............. G06T 7/11; G06T 2207/30204; G06T 7/0012–0016; G06T 2207/10068–10132;
(Continued)

(56) References Cited

U.S. PATENT DOCUMENTS

2016/0005163 A1* 1/2016 Markov ................... G06T 7/11
  382/128
2018/0374194 A1 12/2018 Park et al.
(Continued)

FOREIGN PATENT DOCUMENTS

CN    106097353 A   11/2016
CN    109741317 A    5/2019
(Continued)

OTHER PUBLICATIONS

Corresponding Taiwan office action dated Jan. 18, 2022.

*Primary Examiner* — Atiba O Fitzpatrick
(74) *Attorney, Agent, or Firm* — CKC & Partners Co., LLC

(57) ABSTRACT

An image processing method includes: calculating an area of a first label of a first medical image of a plurality of medical images with a plurality of labels; obtaining a first determination result based on whether the area of the first label is greater than a threshold value; obtaining a second determination result based on whether a second medical image of the medical images adjacent to the first medical image includes a second label overlapping a first projection area of the first label on the second medical image; and selectively deleting the first label on the first medical image according to the first determination result and the second determination result. The present disclosure further provides an image processing system to perform the image processing method.

20 Claims, 8 Drawing Sheets

(51) Int. Cl.
  *G16H 30/20*  (2018.01)
  *G16H 30/40*  (2018.01)
  *G16H 50/70*  (2018.01)
  *A61B 5/00*  (2006.01)
  *A61B 5/055*  (2006.01)
  *A61B 6/03*  (2006.01)
(52) U.S. Cl.
  CPC .............. *A61B 5/055* (2013.01); *A61B 6/032* (2013.01); *A61B 6/037* (2013.01); *G06T 2207/30004* (2013.01); *G16H 50/70* (2018.01)
(58) Field of Classification Search
  CPC ... G06T 2207/30004–30101; G06T 7/10–194; G06T 2207/30096; G06V 10/25; G06V 2201/03–034
  See application file for complete search history.

(56) References Cited

U.S. PATENT DOCUMENTS

2019/0172205 A1\*  6/2019  Mao ..................... G06T 7/0014
2019/0244363 A1   8/2019  Tan et al.

FOREIGN PATENT DOCUMENTS

CN         110110617 A    8/2019
WO    WO-2007048463 A1 \*  5/2007   ............. A61B 5/055

\* cited by examiner

IMAGE PROCESSING METHOD AND SYSTEM FOR SELECTIVELY DELETING LABEL ON MEDICAL IMAGE

CROSS-REFERENCE TO RELATED APPLICATION

This application claims priority to U.S. Provisional Application Ser. No. 62/952,498, filed on Dec. 23, 2019, which is herein incorporated by reference.

BACKGROUND

Field of Invention

This disclosure relates to an image processing method and system, and in particular to a medical image processing method and system capable of increasing marking accuracy.

Description of Related Art

Following the development of technology of machine learning, many models (e.g. object segmentation model) have been used to identify the lesion tissues of the medical images. However, the lesion tissues and the normal tissues (e.g. blood vessel) of the medical images that are provided by the hospital might all be marked in form of bright spot, so that the models, when identifying the lesion tissues of medical images, might generate the result with high false positive rate.

SUMMARY

An aspect of present disclosure relates to an image processing method. The image processing method includes: calculating an area of a first label of a first medical image of a plurality of medical images with a plurality of labels, wherein the medical images are serial section images; obtaining a first determination result based on whether the area of the first label is greater than a threshold value; obtaining a second determination result based on whether a second medical image of the medical images adjacent to the first medical image includes a second label overlapping a first projection area of the first label on the second medical image; and selectively deleting the first label on the first medical image according to the first determination result and the second determination result.

Another aspect of present disclosure relates to an image processing system. The image processing system includes a memory and a processor. The memory is configured to store at least one program code. The processor is configured to execute the at least one program code to perform operations including: calculating an area of a first label of a first medical image of a plurality of medical images with a plurality of labels, wherein the medical images are serial section images; obtaining a first determination result based on whether the area of the first label is greater than a threshold value; obtaining a second determination result based on whether a second medical image of the medical images adjacent to the first medical image includes a second label overlapping a first projection area of the first label on the second medical image; and selectively deleting the first label on the first medical image according to the first determination result and the second determination result.

Another aspect of present disclosure relates to a non-transitory computer readable storage medium. The non-transitory computer readable storage medium includes a computer program to execute an image processing method, wherein the method includes: calculating an area of a first label of a first medical image of a plurality of medical images with a plurality of labels, wherein the medical images are serial section images; obtaining a first determination result based on whether the area of the first label is greater than a threshold value; obtaining a second determination result based on whether a second medical image of the medical images adjacent to the first medical image comprises a second label overlapping a first projection area of the first label on the second medical image; and selectively deleting the first label on the first medical image according to the first determination result and the second determination result.

In summary, the image processing system and the image processing method of the present disclosure are able to delete the incorrect labels by determining whether the area of the first label of the first medical image is greater than the threshold value as well as determining whether the second medical image that is adjacent to the first medical image includes the second label overlapping the projection area of the first label, so as to increase the DICE coefficient. In other words, the probability of false positive is decreased.

It is to be understood that both the foregoing general description and the following detailed description are by examples, and are intended to provide further explanation of the invention as claimed.

BRIEF DESCRIPTION OF THE DRAWINGS

The present disclosure can be more fully understood by reading the following detailed description of the embodiment, with reference made to the accompanying drawings as follows.

DETAILED DESCRIPTION

The embodiments are described in detail below with reference to the appended drawings to better understand the aspects of the present application. However, the provided embodiments are not intended to limit the scope of the disclosure, and the description of the structural operation is not intended to limit the order in which they are performed. Any device that has been recombined by components and produces an equivalent function is within the scope covered by the disclosure.

As used herein, "coupled" and "connected" may be used to indicate that two or more elements physical or electrical contact with each other directly or indirectly, and may also be used to indicate that two or more elements cooperate or interact with each other.

Figure 1:
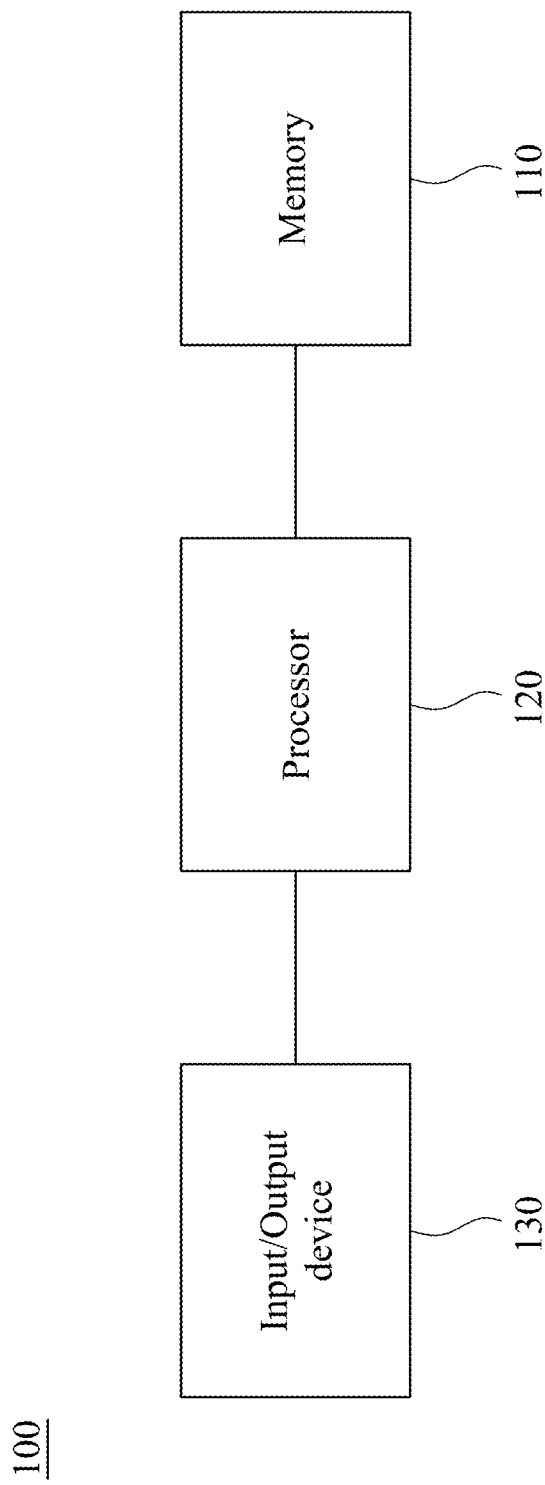
FIG. 1 is a schematic diagram of the image processing system in accordance with some embodiments of the present disclosure.

Referring to FIG. 1, an image processing system 100 in accordance with some embodiments of the present disclosure includes a memory 110, a processor 120 and an input/output (I/O) device 130. The processor 120 is coupled to the memory 110 and the I/O device 130. The image processing system 100 can provide a function for processing a plurality of medical images (referring to FIG. 3) of the human body, so as to reduce the probability of false positive.

The memory 110 is configured to store one or more program codes. The processor 120 is configured to execute the program codes stored in the memory 110 according to one or more input signals, so that a number of operations (e.g. an image processing method 200 as shown in FIG. 2A) can be executed automatically.

In some embodiments, the processor 120 is implemented by one or more central processing unit (CPU), application-specific integrated circuit (ASIC), microprocessor, system on a Chip (SoC) or other suitable processing units. The memory 110 is implemented by a non-transitory computer readable storage medium (e.g. random access memory (RAM), read only memory (ROM), hard disk drive (HDD), solid-state drive (SSD)).

In some embodiments, the I/O device 130 includes a keyboard, a mouse, a touch screen, or a combination thereof, to convert the operations of user to the input signals and transmit the input signals to the processor 120. In some embodiments, the I/O device 130 includes a communication interface (e.g. universal serial bus (USB) interface, Bluetooth interface, Wi-Fi interface, Ethernet interface) to transfer the information or data. In some embodiments, the I/O device 130 includes a screen, a speaker, or a combination thereof, to present the states that are in response to the operations of user.

Figure 2A:
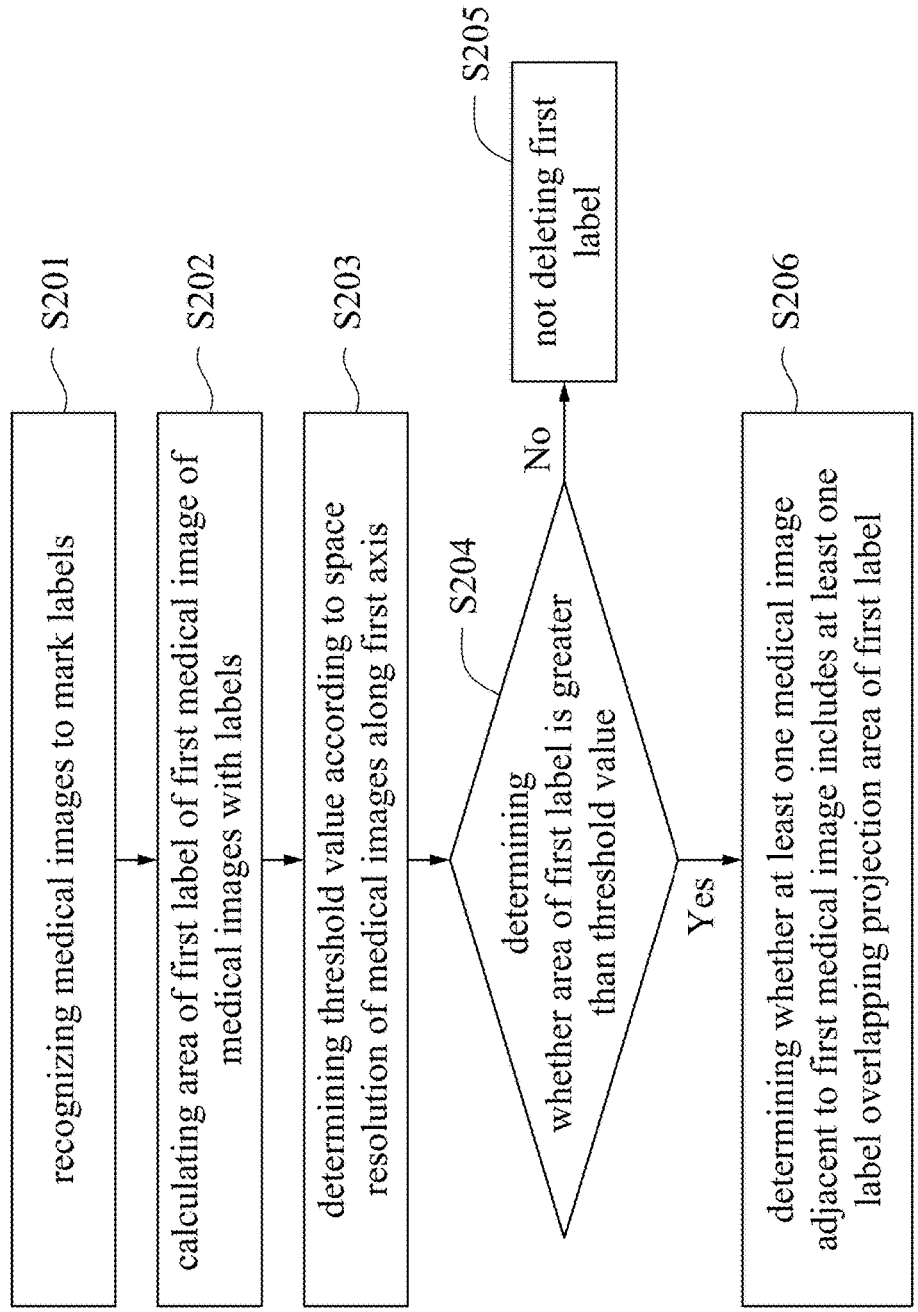
FIG. 2A is a flow diagram of the image processing method according to some embodiments of the present disclosure.
Figure 2B:
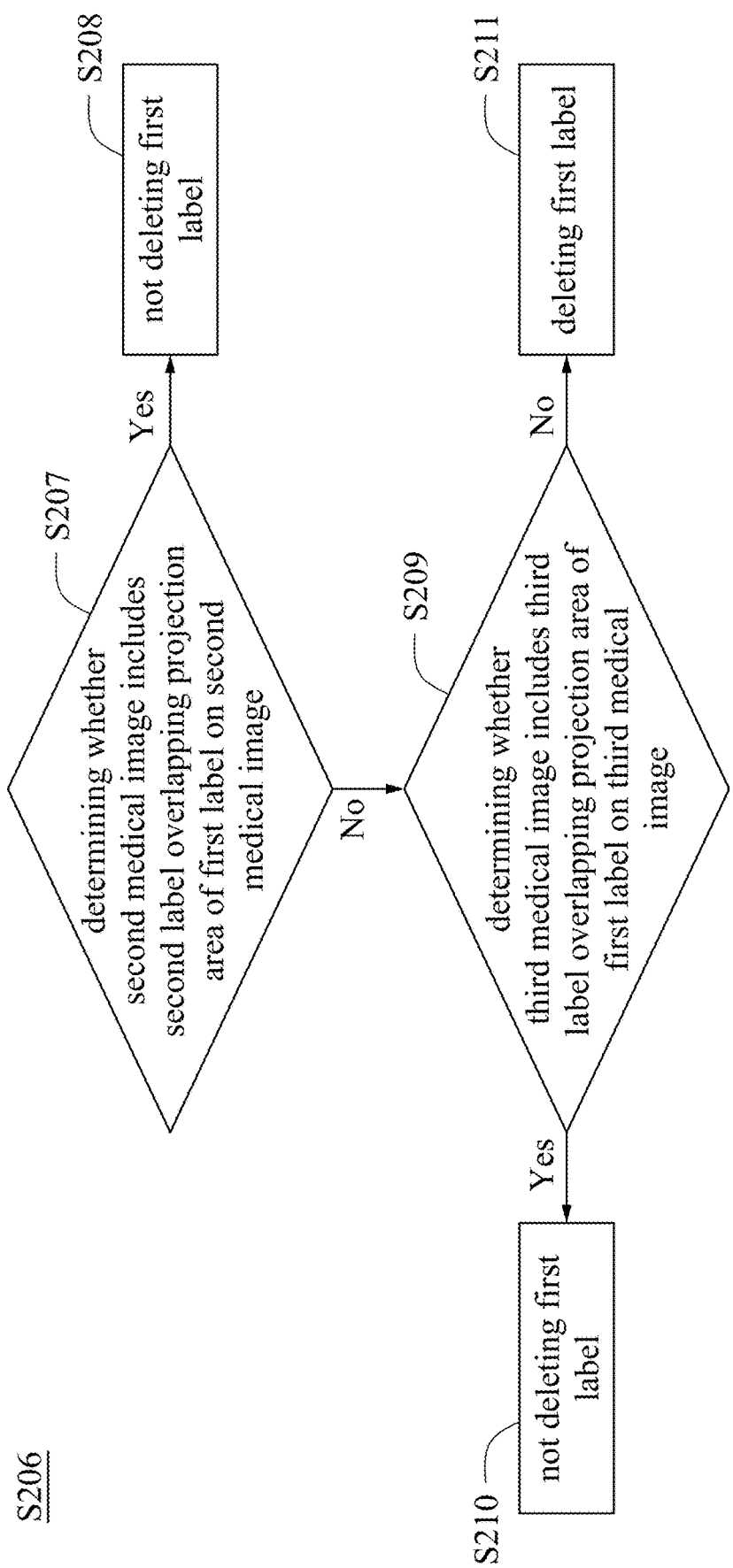
FIG. 2B is a flow diagram of one of the operation of the image processing method according to some embodiments of the present disclosure.

Referring to FIGS. 2A-2B, FIGS. 2A-2B depict an image processing method 200 in accordance with some embodiments of the present disclosure. The image processing method 200 can be performed by processor 120 of FIG. 1. However, the present disclosure should not be limited thereto. As shown in FIG. 2A, the image processing method 200 includes operations S201-S206.

Figure 3:
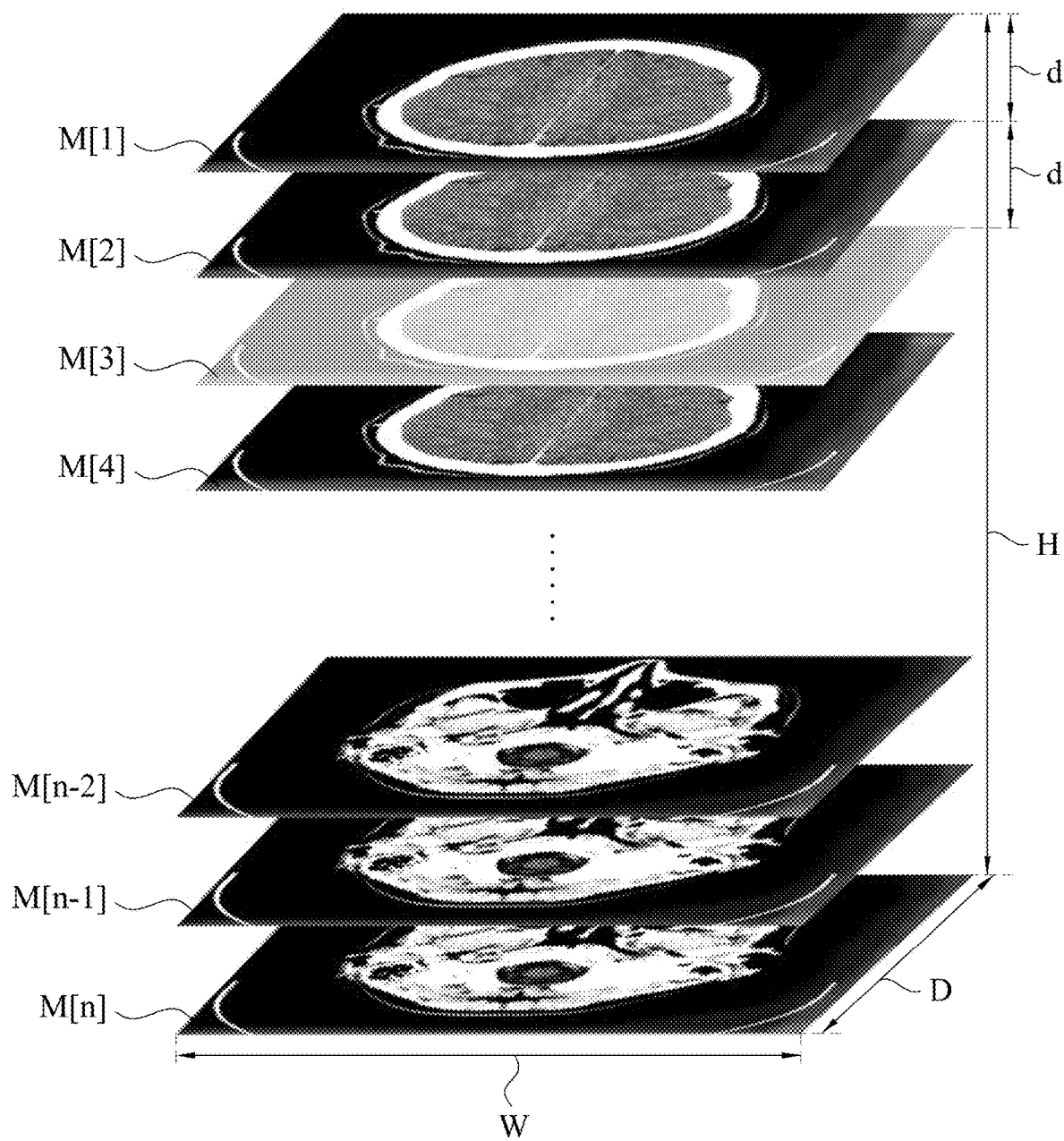
FIG. 3 is a schematic diagram of the medical images in accordance with some embodiments of the present disclosure.

Referring to FIG. 3, FIG. 3 depicts a plurality of medical images M[1]-M[n] which are not marked with any labels. Before the operations S201-S211 are performed, the user can input the medical images M[1]-M[n] through the I/O device 130, and the medical images M[1]-M[n] can be stored in the memory 110 for the processor 120 to process.

The medical images M[1]-M[n] are generated by the medical imaging system (e.g. computed tomography (CT), magnetic resonance imaging (MRI), positron emission tomography (PET), optical coherence tomography (OCT)). As shown in FIG. 3, the medical images M[1]-M[n] are two-dimensional images and may compose a three-dimensional medical image with a predetermined height H, a predetermined width W and a predetermined depth D. For example, the three-dimensional medical image is the three-dimensional image of the human head, and the medical images M[1]-M[n] are the cross-sectional images of the human head at different horizontal levels (that is, serial section images).

Figure 4C:
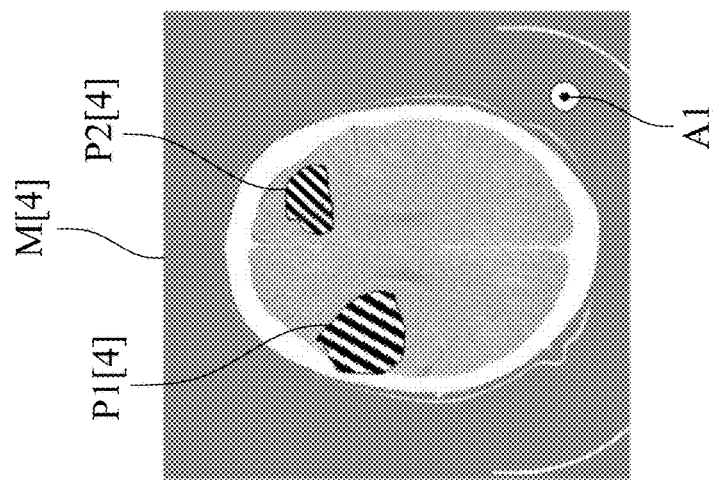
FIGS. 4A-4C are schematic diagrams of the medical images marked with the labels in accordance with some embodiments of the present disclosure.
Figure 4B:
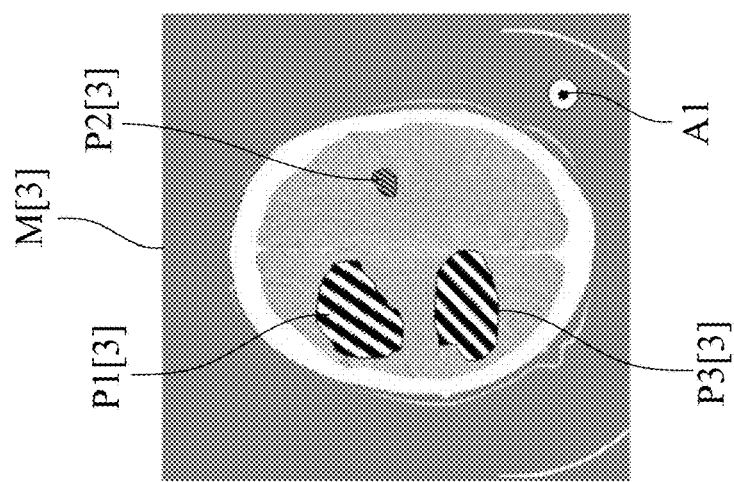
Figure 4A:
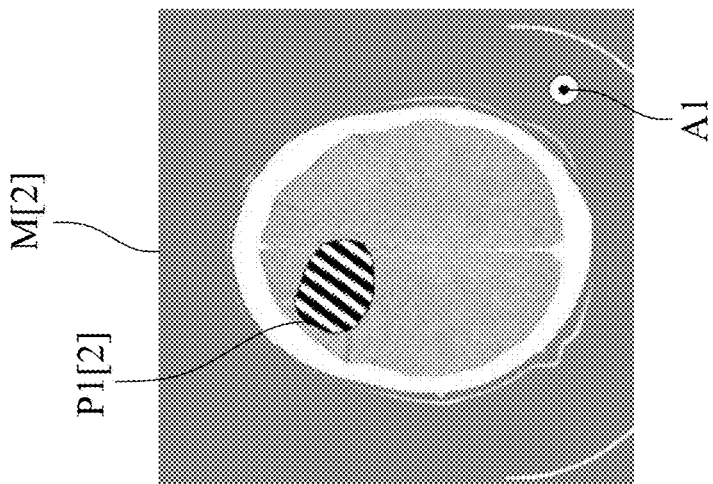

In some embodiments, the medical images M[1]-M[n] has a space resolution in along a first axis A1 (referring to FIGS. 4A-4C). As shown in FIGS. 4A-4C, the first axis A1 (which is represented by a symbol that points upward and leaves the medical images M[2]-M[4]) is perpendicular to each of the medical images M[1]-M[n]. The space resolution of the medical images M[1]-M[n] may be determined by a vertical distance d (as shown in FIG. 3) between two adjacent medical images (e.g. the medical images M[1] and M[2], the medical images M[2] and M[3]). The vertical distance d is the distance parallel to the first axis A1 and is calculated by dividing the predetermined height H by a number n of the medical images M[1]-M[n].

It is worth noting that the space resolution of the medical images M[1]-M[n] is in inverse proportion with the vertical distance d. In other words, the shorter the vertical distance d is, the higher the space resolution is. On the other hand, the longer the vertical distance d is, the lower the space resolution is.

In the operation S201, the processor 120 recognizes the medical images M[1]-M[n] to mark a plurality of labels (referring to FIGS. 4A-4C) on the medical images M[1]-M[n]. For example, as shown in FIG. 4B, the processor 120 recognizes three suspected tissues (represented by the areas filled with oblique lines) from the medical image M[3] by an object segmentation model (e.g. U-Net or C-LSTM of the semantic segmentation, Mask R-CNN of the instance segmentation). Then, the processor 120 marks three labels P1[3], P2[3], P3[3], which are corresponding to the contours of the above-described suspected tissues, on the medical image M[3]. Similarly, as shown in FIGS. 4A and 4C, the processor 120 marks one label P1[2] on the medical image M[2] and two labels P1[4], P2[4] on the medical image M[4].

In some other embodiments, the medical images have been marked with the labels before being inputted to the image processing system 100. Therefore, the operation S201 is omitted.

In some embodiments, since the suspected tissue may include the lesion tissue (e.g. tumor, nodule) and the normal tissue (e.g. blood vessel), some of the labels marked by the processor 120 may correspond to the normal tissue. Therefore, the processor 120 executes the following operations S202-S206 to delete the incorrect labels on the medical images M[1]-M[n] (that is, to delete the labels corresponding to the false positive).

In the operation S202, the processor 120 calculates an area of at least one first label of a first medical image of the medical images. In the example of the medical image M[3] (as shown in FIG. 4B), the processor 120 calculates the area of the surface that is surrounded by the label P1[3]. Similarly, the processor 120 calculates the area of the surface that is surrounded by the label P2[3] and the area of the surface that is surrounded by the label P3[3].

In the operation S203, the processor 120 determines a threshold value according to the space resolution of the medical images M[1]-M[n]. For example, the higher the space resolution is, the smaller the threshold value (e.g. $\pi$ mm$^2$) is. On the other hand, the lower the space resolution is, the greater the threshold value (e.g. $100\pi$ mm$^2$) is. In other words, the threshold value is in inverse proportion with the space resolution. The relationship between the threshold value and the space resolution will be further discussed later.

In the operation S204, the processor 120 determines whether the area of at least one first label is greater than the threshold value to obtain the first determination result and selectively executes the operation S205 or the operation S206 according to the first determination result. Specifically, the processor 120 compares the above-calculated area of each of the labels P1[3]-P3[3] with the threshold value.

In some embodiments, the first determination result shows that the area of the label P2[3] is not greater than the threshold value, hence the processor 120 executes the operation S205. In the operation S205, since the first determination result shows that the area of the label P2[3] is not greater than the threshold value, the suspected tissue corresponding to the label P2[3] may be considered as a lesion tissue (e.g. the tumor with small volume). Accordingly, the processor 120 does not delete (or maintains) the label P2[3].

In some embodiments, the first determination result shows that the area of the label P1[3] (or the label P3[3]) is greater than the threshold value, hence the processor 120 executes the operation S206. In the operation S206, since the first determination result shows that the area of the label P1[3] (or the label P3[3]) is greater than the threshold value, the suspected tissue corresponding to the label P1[3] (or the label P3[3]) is still doubted to be a lesion tissue or a normal tissue. Accordingly, the processor 120 further determines whether at least one medical image (e.g. medical image M[2], medical image M[4]) adjacent to the first medical image includes at least one label overlapping a projection area of the first label (e.g. the label P1[3], the label P3[3]) or not.

As shown in FIG. 2B, the operation S206 includes the operations S207-S211. In the operation S207, the processor 120 determines whether a second medical image includes a second label overlapping the projection area of the first label on the second medical image. In such way, the processor 120 obtains the second determination result and selectively executes the operation S208 or the operation S209 according to the second determination result.

Figure 5B:
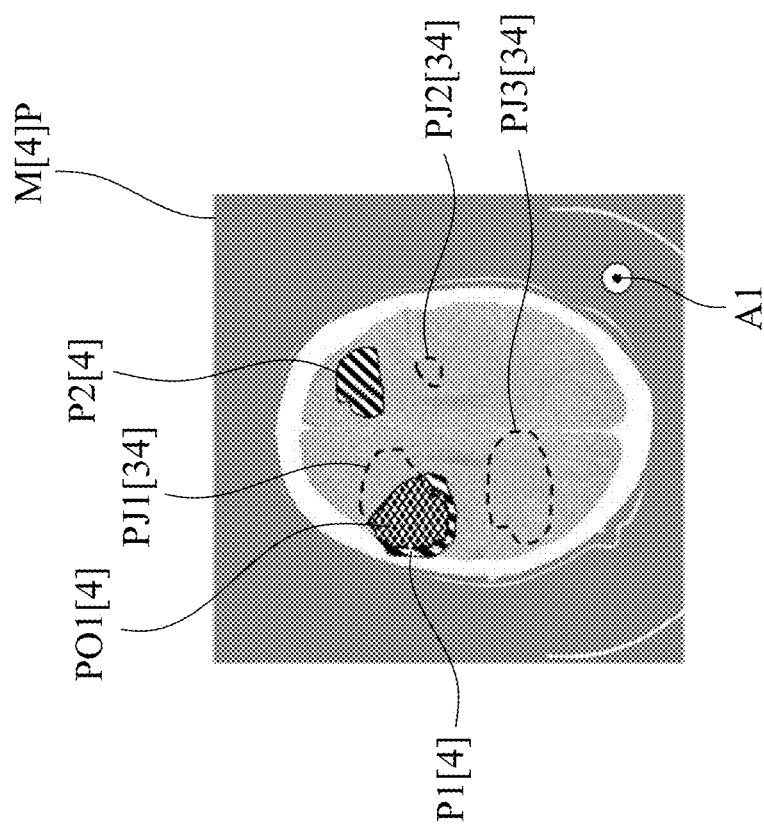
FIGS. 5A-5B are schematic diagrams of the adjacent medical images on which the projection areas of the labels of the medical image of FIG. 4B are formed.
Figure 5A:
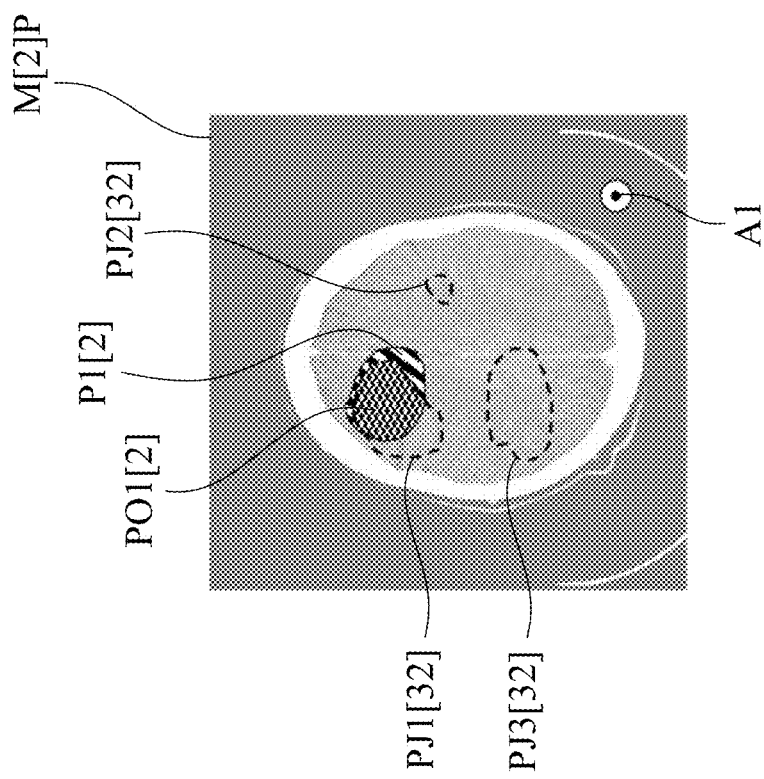

Referring to FIGS. 5A and 5B, FIGS. 5A and 5B depict that the projection areas of the labels P1[3]-P3[3] of the first medical image are formed on two adjacent medical images. In the example of the label P1[3], the label P1[3] is projected in the direction parallel to the first axis A1, so as to form a projection area PJ1[32] on the medical image M[2]P and a projection area PJ1[34] on the medical image M[4]P. Similarly, the labels P2[3], P3[3] of the medical image M[3] may be projected to form the projection areas PJ2[32], PJ3[32] on the medical image M[2]P and the projection areas PJ2[34], PJ3[34] on the medical image M[4]P. As shown in FIG. 5A, the projection area PJ1[32] overlaps the label P1[2] on the medical image M[2]P, so that an overlap area P01[2] (represented by the area filled with black and white squares) is generated. As shown in FIG. 5B, the projection area PJ1[34] overlaps the label P1[4] on the medical image M[4]P, so that an overlap area P01[4] (represented by the area filled with black and white squares) is generated.

Regarding to the label P1[3], in some embodiments, the processor 120 may determine that the medical image M[2]P includes the label P1[2] overlapping the projection area PJ1[32] of the label P1[3], so as to execute the operation S208. In some other embodiments, the processor 120 may determine that the medical image M[4]P includes the label P1[4] overlapping the projection area PJ1[34] of the label P1[3], so as to execute the operation S208.

In the operation S208, since the second determination result shows that the second medical image (e.g. medical image M[2]P or medical image M[4]P) includes the second label (e.g. the label P1[2] or the label P1[4]) overlapping the projection area (e.g. the projection area PJ1[32] corresponding to the medical image M[2]P or the projection area PJ1[34] corresponding to the medical image M[4]P) of the first label (e.g. the label P1[3]), the suspected tissue corresponding to the label P1[3] is considered as a lesion tissue (e.g. the tumor with great volume). Accordingly, the processor 120 does not delete (or maintains) the label P1[3].

Regarding to the label P3[3], in some embodiments, the processor 120 may determine that the medical image M[2]P includes no label overlapping the projection area PJ3[32] of the label P3[3], so as to execute the operation S209. In some other embodiments, the processor 120 may determine that the medical image M[4]P includes no label overlapping the projection area PJ3[34] of the label P3[3], so as to execute the operation S209.

In the operation S209, since the second determination result shows that the second medical image (e.g. medical image M[2]P or medical image M[4]P) does not include second label overlapping the projection area (e.g. the projection area PJ3[32] corresponding to the medical image M[2]P or the projection area PJ3[34] corresponding to the medical image M[4]P) of the first label (e.g. the label P3[3]), the suspected tissue corresponding to the label P3[3] is still doubted to be a lesion tissue or a normal tissue. Accordingly, the processor 120 further determines whether a third medical image includes a third label overlapping another projection area of the first label or not. In such way, the processor 120 obtains the third determination result and selectively executes the operation S210 or the operation S211 according to the third determination result.

In some embodiments, the processer 120 determines that the medical image M[2]P (regarding as the second medical image) does not include the second label overlapping the projection area of the first label, but also determines that the medical image M[4]P (regarding as the third medical image) includes the third label overlapping the another projection area of the first label, so as to execute the operation S210. In some other embodiments, the processer 120 determines that the medical image M[4]P (regarding as the second medical image) does not include the second label overlapping the projection area of the first label, but also determines that the medical image M[2]P (regarding as the third medical image) includes the third label overlapping the another projection area of the first label, so as to execute the operation S210.

In the operation S210, since the third determination result shows that the third medical image (e.g. medical image M[2]P, medical image M[4]P) includes the third label overlapping the another projection area of the first label, the suspected tissue corresponding to the first label is considered as a lesion tissue (e.g. the tumor with great volume). Accordingly, the processor 120 does not delete (or maintains) the first label.

In brief, the processor 120 maintains the first label when at least one adjacent medical image includes at least one label overlapping the projection area of the first label. However, in some other embodiments, the processor 120 may maintain the first label if two adjacent medical images (e.g. the medical images M[2]P and M[4]P) include the second label and the third label respectively overlapping two projection areas of the first label on two adjacent medical images.

In the example of determining the label P3[3] (referring to FIGS. 5A and 5B), the processer 120 determines that the medical image M[2]P includes no label overlapping the projection area PJ3[32] of the label P3[3], and also determines that the medical image M[4]P includes no label overlapping the another projection area PJ3[34] of the label P3[3], so as to execute the operation S211.

In the operation S211, since the third determination result shows that the third medical image (e.g. medical image M[2]P, medical image M[4]P) does not include the third label overlapping the another projection area (e.g. the projection area PJ3[32], the projection area PJ3[34]) of the first label (e.g. the label P3[3]), the suspected tissue corresponding to the label P3[3] is considered as a normal tissue (because the lesion tissue is usually spherical and rarely flat). Accordingly, the processor 120 deletes the label P3[3].

Figure 6:
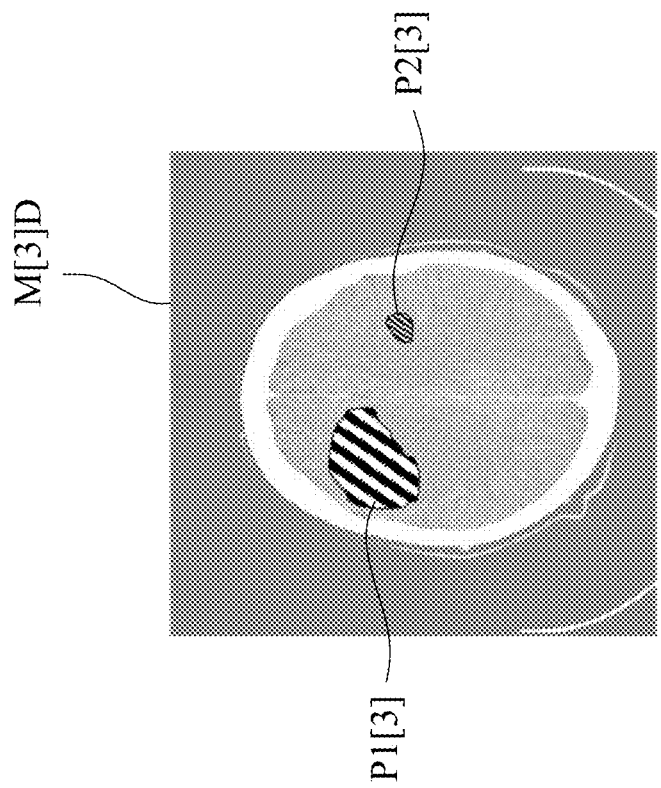
FIG. 6 is a schematic diagram of the medical image of FIG. 4B after being processed.

Referring to FIG. 6, after executing the operations S202-S211, the processor 120 generates the processed medical image M[3]D and would process the medical image M[4]. In some embodiments, the processor 120 sequentially processes the unprocessed medical images M[1]-M[n] to delete the incorrect labels.

In some embodiments, when processing the medical image M[1] or M[n], the processor 120 may only determine one medical image M[2] or M[n−1] that is adjacent to the medical image M[1] or M[n]. Accordingly, when the medical image M[2] or M[n−1] includes the second label overlapping the projection area of the first label of the medical image M[1] or M[n], the processor 120 maintains the first label. When the medical image M[2] or M[n−1] does not include the second label overlapping the projection area of the first label of the medical image M[1] or M[n], the processor 120 deletes the first label.

Figure 7B:
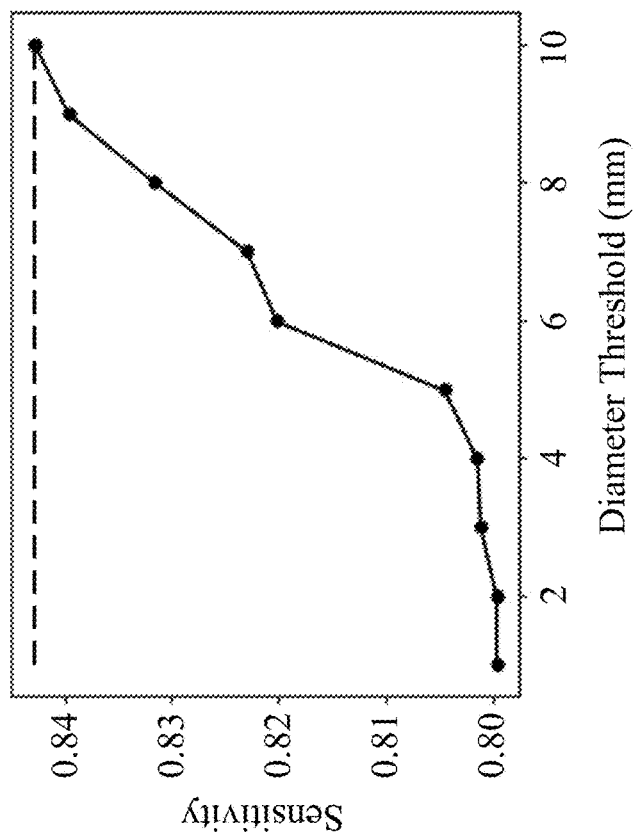
FIG. 7B is a relation curve diagram of the sensitivity and the diameter threshold in accordance with some embodiments of the present disclosure.
Figure 7A:
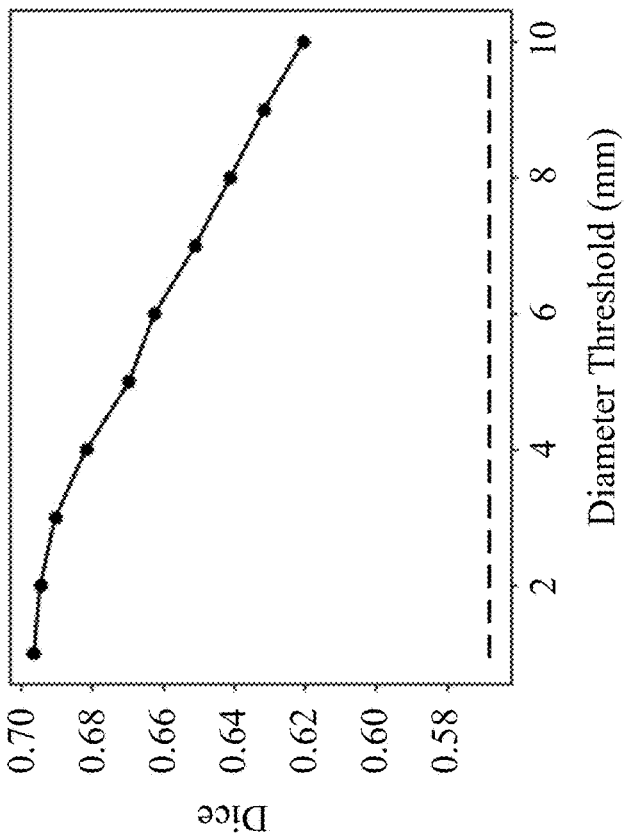
FIG. 7A is a relation curve diagram of the DICE coefficient and the diameter threshold in accordance with some embodiments of the present disclosure.

Referring to FIGS. 7A-7B, FIG. 7A depicts the relation between the DICE coefficient and the diameter threshold, and FIG. 7B depicts the relation between the sensitivity and the diameter threshold. The DICE coefficient can be used to compare the similarity of different sets (e.g. the first set of the lesion tissues (identified by the skilled doctors) and the second set of the labels (recognized through the object segmentation model)). Basically, the higher the DICE coefficient is, the lower the probability of false positive. The sensitivity is the probability of the lesion tissue that is marked with the label (that is, the probability of true positive). The threshold value may be defined by the area of the circular surface with the diameter threshold. For example, if the diameter threshold is 10 mm, the threshold value is $25\pi$ mm$^2$. In some embodiment, the DICE coefficient and the sensitivity can be represented as the following equations (1) and (2):

$$D = \frac{2 \times |G \cap P|}{|G| + |P|}; \quad (1)$$

and $$S = \frac{|G \cap P|}{|G|}, \quad (2)$$

where D is the DICE coefficient, S is the sensitivity, G is the area of the actual lesion tissues of the medical images M[1]-M[n], and P is the area of the labels on the medical images M[1]-M[n].

Before the incorrect labels are deleted, the DICE coefficient is substantially 56.82% (referring to the broken line as shown in FIG. 7A). The sensitivity is substantially 84.27% (referring to the broken line as shown in FIG. 7B). After the operations S202-S211 are executed to delete the incorrect labels, the DICE coefficient may be varied in the range of 62.05% to 69.65% (referring to the solid line as shown in FIG. 7A) according to the length of the diameter threshold. The sensitivity may be varied in the range of 79.97% to 84.27% (referring to the solid line as shown in FIG. 7B) according to the length of the diameter threshold. As shown in FIGS. 7A and 7B, when the diameter threshold is 10 mm, the DICE coefficient is increased by 5.23%, and the sensitivity is unchanged. When the diameter threshold is 1 mm, the DICE coefficient is increased by 12.83%, and the sensitivity is slightly decreased by 4.3% (since the sensitivity cannot be increased after the operations S202-S211 are executed).

As set forth above, the threshold value is determined according to the space resolution of the medical images M[1]-M[n]. Besides, the threshold value is also determined according to the desire for the DICE coefficient and the sensitivity. If a high degree of DICE coefficient is desired, the threshold value should be decreased (for example, the diameter threshold should be 1 mm) to delete more incorrect labels (in other words, to increase the DICE coefficient significantly). By contrast, if a high degree of sensitivity is desired, the threshold value should be increased (for example, the diameter threshold should be 10 mm) to delete incorrect labels (in other words, to increase the DICE coefficient slightly) while the sensitivity is maintained.

In summary, by determining whether the area of the first label of the first medical image is greater than the threshold value as well as determining whether at least one second medical image that is adjacent to the first medical image includes the second label overlapping the projection area of the first label, the image processing system 100 and the image processing method 200 of the present disclosure are able to delete the incorrect labels, so that the DICE coefficient is increased. In other words, the probability of false positive is decreased.

Methods for information distribution, may take the form of a program code (i.e., executable instructions) embodied in tangible media, such as floppy diskettes, CD-ROMS, hard drives, or any other non-transitory computer readable storage medium, wherein, when the program code is loaded into and executed by a computer, the computer thereby becomes an apparatus for practicing the methods. The methods may also be embodied in the form of a program code transmitted over some transmission medium, such as electrical wiring or cabling, through fiber optics, or via any other form of transmission, wherein, when the program code is received and loaded into and executed by a computer, the computer becomes an apparatus for practicing the disclosed methods. When implemented on a general-purpose processor, the program code combines with the processor to provide a unique apparatus that operates analogously to application specific logic circuits.

Although the present disclosure has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present disclosure without departing from the scope or spirit of the invention. In view of the foregoing, it is intended that the present invention cover modifications and variations of this invention provided they fall within the scope of the following claims.

What is claimed is:

1. An image processing method comprising:

calculating an area of a first label of a first medical image of a plurality of medical images with a plurality of labels, wherein the medical images are serial section images;

obtaining a first determination result based on whether the area of the first label is greater than a threshold value;

obtaining a second determination result based on whether a second medical image of the medical images adjacent to the first medical image comprises a second label overlapping a first projection area of the first label on the second medical image; and in response to determining that the area of the first label is greater than the threshold value and then determining that the second medical image does not comprise the second label overlapping the first projection area of the first label on the second medical image, deleting the first label.

2. The image processing method of claim 1, wherein after the operation of obtaining the second determination result based on whether the second medical image of the medical images adjacent to the first medical image comprises the second label overlapping the first projection area of the first label on the second medical image, the method further comprises:

obtaining a third determination result based on whether a third medical image of the medical images adjacent to the first medical image comprises a third label overlapping a second projection area of the first label on the third medical image.

3. The image processing method of claim 2, wherein after the operation of obtaining the third determination result based on whether the third medical image of the medical images adjacent to the first medical image comprises the third label overlapping the second projection area of the first label on the third medical image, the method further comprises:

deleting the first label in response to a determination result that the area of the first label is greater than the threshold value, the second medical image does not comprise the second label and the third medical image does not comprise the third label.

4. The image processing method of claim 2, wherein after the operation of obtaining the third determination result based on whether the third medical image of the medical images adjacent to the first medical image comprises the third label overlapping the second projection area of the first label on the third medical image, the method further comprises:

maintaining the first label in response to a determination result that the area of the first label is greater than the threshold value, the second medical image does not comprise the second label and the third medical image comprises the third label.

5. The image processing method of claim 1, wherein the operation of obtaining the second determination result based on whether the second medical image of the medical images adjacent to the first medical image comprises the second label overlapping the first projection area of the first label on the second medical image is performed in response to the first determination result showing that the area of the first label is greater than the threshold value.

6. The image processing method of claim 1, further comprising:

maintaining the first label in response to a determination result that the area of the first label is greater than the threshold value and the second medical image comprises the second label.

7. The image processing method of claim 1, further comprising:

maintaining the first label in response to a determination result that the area of the first label is not greater than the threshold value.

8. The image processing method of claim 1, wherein before the operation of calculating the area of the first label of the first medical image of the medical images with the labels, the method further comprises:

recognizing the medical images to mark the labels.

9. The image processing method of claim 1, wherein before the operation of obtaining the first determination result based on whether the area of the first label is greater than the threshold value, the method further comprises:

determining the threshold value according to a space resolution of the medical images along a first axis, wherein the first axis is perpendicular to the first medical image and the second medical image, and the first label is projected onto the second medical image along the first axis to form the first projection area.

10. The image processing method of claim 9, wherein the threshold value is in inverse proportion with the space resolution, and the space resolution is in inverse proportion with a vertical distance between the first medical image and the second medical image.

11. The image processing method of claim 1, wherein before the operation of obtaining the first determination result based on whether the area of the first label is greater than the threshold value, the method further comprises:

determining the threshold value according to a sensitivity and a DICE coefficient.

12. An image processing system, comprises:

a memory configured to store at least one program code; and a processor configured to execute the at least one program code to perform operations comprising:

calculating an area of a first label of a first medical image of a plurality of medical images with a plurality of labels, wherein the medical images are serial section images;

obtaining a first determination result based on whether the area of the first label is greater than a threshold value;

obtaining a second determination result based on whether a second medical image of the medical images adjacent to the first medical image comprises a second label overlapping a first projection area of the first label on the second medical image; and in response to determining that the area of the first label is greater than the threshold value and then determining that the second medical image does not comprise the second label overlapping the first projection area of the first label on the second medical image, deleting the first label.

13. The image processing system of claim 12, wherein after the operation of obtaining the second determination result based on whether the second medical image of the medical images adjacent to the first medical image comprises the second label overlapping the first projection area of the first label on the second medical image, the processor further performs:

obtaining a third determination result based on whether a third medical image of the medical images adjacent to the first medical image comprises a third label overlapping a second projection area of the first label on the third medical image.

14. The image processing system of claim 13, wherein the processor deletes the first label in response to a determination result that the area of the first label is greater than the threshold value, the second medical image does not comprise the second label and the third medical image does not comprise the third label.

15. The image processing system of claim 13, wherein the processor maintains the first label in response to a determination result that the area of the first label is greater than the threshold value, the second medical image does not comprise the second label and the third medical image comprises the third label.

16. The image processing system of claim 12, wherein the processor maintains the first label in response to a determination result that the area of the first label is greater than the threshold value and the second medical image comprises the second label.

17. The image processing system of claim 12, wherein the processor maintains the first label in response to a determination result that the area of the first label is not greater than the threshold value.

18. The image processing system of claim 12, wherein before the operation of obtaining a first determination result based on whether the area of the first label is greater than a threshold value or not, the processor further performs:

determining the threshold value according to a space resolution of the medical images along a first axis, wherein the first axis is perpendicular to the first medical image and the second medical image, and the first label is projected onto the second medical image along the first axis to form the first projection area.

19. The image processing system of claim 18, wherein the threshold value is in inverse proportion with the space resolution, and the space resolution is in inverse proportion with a vertical distance between the first medical image and the second medical image.

20. A non-transitory computer readable storage medium with a computer program to execute an image processing method, wherein the method comprises:

calculating an area of a first label of a first medical image of a plurality of medical images with a plurality of labels, wherein the medical images are serial section images;

obtaining a first determination result based on whether the area of the first label is greater than a threshold value;

obtaining a second determination result based on whether a second medical image of the medical images adjacent to the first medical image comprises a second label overlapping a first projection area of the first label on the second medical image; and in response to determining that the area of the first label is greater than the threshold value and then determining that the second medical image does not comprise the second label overlapping the first projection area of the first label on the second medical image, deleting the first label.

* * * * *